United States Patent [19]
Morales et al.

[11] Patent Number: 5,888,986
[45] Date of Patent: Mar. 30, 1999

[54] METHOD FOR TREATING THE URINARY BLADDER AND ASSOCIATED STRUCTURES USING HYALURONIC ACID

[75] Inventors: Alvaro Morales, Kingston; Stanley J. Alkemade, Arva, both of Canada

[73] Assignee: Bioniche Inc., Canada

[21] Appl. No.: 644,438

[22] Filed: May 13, 1996

Related U.S. Application Data

[63] Continuation-in-part of Ser. No. 591,015, Feb. 8, 1996, and Ser. No. 388,038, Feb. 14, 1995, Pat. No. 5,591,724.

[51] Int. Cl.$^6$ .................................................. A61K 31/725
[52] U.S. Cl. ............................ 514/54; 514/771; 514/891; 536/55.1; 536/123.1
[58] Field of Search ............................ 514/54, 777, 891; 536/55.1, 123.1

[56] References Cited

U.S. PATENT DOCUMENTS

| | | |
|---|---|---|
| 4,141,973 | 2/1979 | Balazs . |
| 4,296,104 | 10/1981 | Herschler . |
| 4,302,577 | 11/1981 | Rucker . |
| 4,524,066 | 6/1985 | Wolf . |
| 4,640,912 | 2/1987 | Hausman . |
| 4,711,780 | 12/1987 | Fahim . |
| 4,820,693 | 4/1989 | Gillespie . |
| 4,879,282 | 11/1989 | Saliba, Jr. . |
| 4,966,890 | 10/1990 | Gillespie . |
| 5,037,810 | 8/1991 | Saliba, Jr. . |
| 5,180,715 | 1/1993 | Parsons . |

FOREIGN PATENT DOCUMENTS

| | | |
|---|---|---|
| 0 572 932 A2 | 8/1993 | European Pat. Off. . |
| WO 94/21299 | 9/1994 | WIPO . |

OTHER PUBLICATIONS

Stewart et al., "The Use of Dimethyl Sulfoxide (DMSO) in the Treatment of Interstitial Cystitis," *J. Urology*, vol. 98, pp. 671–672 (1968).
Parsons et al., "Decreased Urinary Uronic Acid Levels in Individuals with Interstitial Cystitis," *J. Urology*, vol. 143, pp. 690–693 (1990).
Fleischmann et al., "Clinical and Immunological Response to Nifedipine for the Treatment of Interstitial Cystitis," *J. Urology*, vol. 146, pp. 1235–1239 (1991).
Nickel et al., "The Bladder Mucus (Glycosaminoglycan) Layer in Interstitial Cystitis," *J. Urology*, vol. 149, pp. 716–718 (1993).
Hanno et al., "Conservative Therapy of Interstitial Cystitial," *Seminars in Urology*, vol. 9, No. 2, pp. 143–147 (1991).
Chelsky et al., "Bladder Permeability in Interstitial Cystitis is Similar to that of Normal Volunteers: Direct Measurement by Transvesical Absorption of 99mTechnetiumdiethylenetri-aminepentaacetic Acid," *J. Urology*, vol. 151, pp. 346–349 (1994).

Eldrup et al., "Permeability and Ultrastructure of Human Bladder Epithelium," *Br. J. Urology*, vol. 55, pp. 488–492 (1983).
Brandt, "The Effect of Synovial Hyaluronate on the Injestion of Monosodium Urate Crystals by Leukocytes," *Clinica Chimica Acta*, vol. 55, pp. 307–315 (1974).
Messing et al., "Interstitial Cystitis," *Urology*, vol. 12, No. 4, pp. 381–392 (1978).
Balazs et al., "The Effect of Hyaluronic Acid on Fibroblasts, Mononuclear Phagocytes and Lyphocytes," *Biology of Fibroblasts*, Academic Press, pp. 237–252 (1973).
Kuwahara et al., "Bacterial Infection and Acid Mucopolysaccharides in Epithelium of Rat Urinary Bladder," *Urological Research*, vol. 10, No. 2, pp. 93–96 (1982).
Gill et al., "Protective Effects of Heparin and Other Sulfated Glycosaminoglycans on Crystal Adhesion to Injured Urothelium," *J. Urology*, vol. 127(1), pp. 152–154 (1982).
Maroudas, N.G. et al., "Polymer Treatments Reduce Adhesion of Comminuted Store in Rat Bladder," *British Journal of Urology*, vol. 59(6), pp. 519–522 (1987).
Laurent, C. et al., "Localization and Quantity of Hyaluronan in Urogenital Organs of Male and Female Rats," *Cell & Tissue Research*, vol. 279(2), pp. 241–248 (1995).
Holm–Bentzen, Merete et al., "Glycosaminoglycans on the Surface of the Human Urothelium: A Preliminary Report," *Neurology and Urodynamics*, vol. 5(6), pp. 519–523 (1986).
Wakatsuki, Akira et al., "Possible Role of Hyaluronate in Experimental Renal Stone Formation in Rabbits," *Journal of Urology*, vol. 133(2), pp. 319–323 (1985).
Hurst, Robert E. et al., "Functional and Structural Characteristics of the Glycosaminoglycans of the Bladder Luminal Surface," *J. Urology*, vol. 138(2), pp. 433–437 (1987).
The Merck Index, 11th Ed., p. 7093 at 7090 (1989).
Strohmaier, W.L., "Therapie Der Interstitiellen Bzm. Radiogenen Zystitis Mit D–Glukosamin," *Hel. Chir. Acta*, vol. 56, pp. 323–325 (1989).
Kiesewetter, E. et al., "Einfluß der Hyaluronsäure auf eine schwere Harnwegsinfektion bei idiopathischer Hyperkalzurie," *Z.Urologie und Nephrologie*, vol. 58(10), pp. 735–738 (1965).
Perez–Marrero, R., et al., "A Controlled Study of Dimethyl Sulfoxide in Interstitial Cystitis," *Journal of Urology*, vol. 140, pp. 36–39 (1988).
Wein, A.J., et al., "Interstitial Cystitis; Current and Future Approaches to Diagnosis and Treatment," *Urologic Clinics of North America*, vol. 21, No. 1, pp. 153–161 (1994).

*Primary Examiner*—Shep K. Rose
*Attorney, Agent, or Firm*—Jones & Askew

[57] ABSTRACT

A method of treating interstitial cystitis comprising contacting the transitional epithelium lining the urinary bladder and associated structures in a mammal having interstitial cystitis with a solution containing hyaluronic acid having a average molecular weight of not less than $2\times10^5$ Daltons in a concentration effective to treat the interstitial cystitis.

7 Claims, 1 Drawing Sheet

% Reduction of Symptoms per Treatment Group at 4, 8 and 12 Weeks

METHOD FOR TREATING THE URINARY BLADDER AND ASSOCIATED STRUCTURES USING HYALURONIC ACID

CROSS-REFERENCE TO RELATED APPLICATIONS

This application is a continuation-in-part of U.S. patent application Ser. No. 08/591,015 filed Feb. 8, 1996 and of U.S. patent application Ser. No. 08/388,038 filed Feb. 14, 1995, now U.S. Pat. No. 5,591,724.

TECHNICAL FIELD

The present invention relates to a novel method for treating the urinary bladder and associated structures in a mammal comprising the step of contacting the urinary bladder and associated structures in the mammal with a solution containing hyaluronic acid having an average molecular weight of not less than $2 \times 10^5$ Daltons in a concentration effective to treat the interstitial cystitis. More particularly, the present invention relates to a novel method for treating the urinary bladder and associated structures in a mammal having interstitial cystitis comprising the step of contacting the transitional epithelium lining the urinary bladder and associated structures in the mammal having interstitial cystitis with a solution containing hyaluronic acid having an average molecular weight of $5 \times 10^5$ to $3.1 \times 10^6$ Daltons in a concentration effective to treat the interstitial cystitis.

BACKGROUND OF THE INVENTION

In mammals, the unique tight junctions of urinary bladder surface epithelial cells are the fundamental mechanism by which the urinary bladder maintains it impermeability. However, the glycosaminoglycan layer on the luminal surface of the urinary bladder wall may be an important defense mechanism for protecting the transitional epithelium from urinary irritants (Chelsky, M. et al. 1994. Journal of Urology, 151:346). This glycosaminoglycan layer consists of mucopolysaccharides attached to a core protein that, in turn, is bound to a central hyaluronic acid string. This highly viscous, highly hydrophilic glycosaminoglycan layer may protect the transitional epithelium of the urinary bladder from irritants in the urine including, but not limited to, pathogens, microcrystals, proteins, calcium and carcinogens (Nickel, J. C. et al. 1993. Journal of Urology, 149:716). This glycosaminoglycan layer also may prevent small, uncharged molecules such as urea from diffusing to and across the transitional cell epithelium. Thus, the glycosaminoglycan layer lining the urinary bladder may act as a barrier between the environment within the lumen of the urinary bladder and the transitional epithelium of the urinary bladder and may protect this transitional epithelium from inflammation, infection, trauma, stone formation and carcinogenesis.

Interstitial cystitis is a poorly understood bladder condition for which there is no universal effective treatment program (Fleischmann, J. D. et al. 1991. Journal of Urology, 146:1235). Symptoms include urgency for urination, increased frequency of urination and suprapubic pain usually relieved by voiding. Other symptoms include arthritis, spastic colon and low grade fever. Individuals with interstitial cystitis can be significantly disabled, and individuals with advanced interstitial cystitis can require major surgery in order to function. Although the etiology of interstitial cystitis remains unexplained, it has been suggested that abnormalities of or deficiencies in the glycosaminoglycan layer lining the transitional epithelium of the bladder may be a primary defect. (Eldrup J. 1983. British Journal of Urology, 55:488). These abnormalities or deficiencies may enable increased permeability of the transitional epithelium (Parsons, E. L. et al. 1990. Journal of Urology, 143:690) and this increased permeability may enable urinary solutes to gain access to the subepithelial tissue and to induce an irritative, inflammatory response that contributes to the symptoms of interstitial cystitis.

There is no standard treatment for interstitial cystitis. Among the treatments used are hydraulic distention of the urinary bladder, oral amitriptyline or sodium pentosanpolysulfate, intravesical instillation of dimethylsulfoxide, oxychlorosene sodium, silver nitrate, heparin, or a composition comprising an angiostatic steroid and pentosanpolysulfate. However, the efficacy of these treatments is variable.

Hydraulic distention of the urinary bladder is done under general or spinal anesthesia for one to two minutes at a pressure of 80 to 100 cm $H_2O$. In one study using hydraulic distention of the urinary bladder to treat interstitial cystitis, less than 55% of the patients treated reported relief immediately after treatment and only 2% reported relief six months after treatment (Hanno P. M. et al. 1991. Semin Urology, 9:143)

Instillation of dimethylsulfoxide (DMSO) into the urinary bladder for six to eight weeks resulted in a 53% response rate to DMSO versus an 18% response rate to placebo, with the average length of response being six months (Perez-Marrero, R. et al. 1967. Journal of Urology, 98:671). Pharmacological effects of DMSO include membrane penetration, enhanced drug absorption, anti-inflammatory and analgesic effects, collagen dissolution, muscle relaxation and mast cell histamine release. Side effects include increased vesical irritability and garlic-like breath odor. Equivalent results to instillation of DMSO have been reported with oxychlorosene sodium (Messing, E. M. et al. 1978. Urology, 12:381). However instillation of oxychlorosene sodium requires anesthesia because of intense discomfort.

Sodium pentosanpolysulfate is a low molecular weight synthetic glycosaminoglycan (U.S. Pat. No. 4,524,066 to Wolf) and is characterized by very low viscosity and high electronegativity.

U.S. Pat. No. 4,820,693 to Gillespie (Gillespie '693) discloses a composition and method for arresting angiogenesis and cell, capillary or membrane leakage comprising either oral or intravesical administration of an angiostatic steroid and pentosanpolysulfate. The molecular weight of pentosanpolysulfate is between $1.5 \times 10^3$ and $5 \times 10^3$ Daltons (The Merck Index, 11th Edition. 1989. p. 7093 at 7090). The molecular weight of the pentosanpolysulfate claimed in Gillespie '693 is between $1.6 \times 10^3$ and $6 \times 10^3$ Daltons, and is preferably about $2 \times 10^3$ Daltons. U.S. Pat. No. 4,966,890 to Gillespie (Gillespie '890) discloses a composition and method for treating interstitial cystitis comprising either oral or intravesical administration of an angiostatic steroid and pentosanpolysulfate. Gillespie '890 teaches that pentosanpoiysulfate can be used in place of heparin and that pentosanpolysulfate, in combination with an angiostatic steroid, cures interstitial cystitis by arresting angiogenesis, cell membrane leakage and capillary leakage or exchange in the urinary bladder.

U.S. Pat. No. 5,180,715 to Parsons (Parsons '715) also discloses the use of pentosanpolysulfate for treating interstitial cystitis. Parsons '715 provides data to show that oral pentosanpolysulfate at doses in excess of 100 mg per day are most effective for treating interstitial cystitis. Parsons '715 also suggests, but provides no data to show, that intravesical instillation of pentosanpolysulfate is useful for treating interstitial cystitis. Parsons '715 teaches that pentosanpolysulfate can be used in place of heparin and that pentosanpolysulfate acts to block bacterial adherence to the transitional epithelium of the urinary bladder.

Pentosanpolysulfate as disclosed in Gillespie '693, in Gillespie '890 and in Parsons '715 is a low viscosity glycosaminoglycan. As interstitial cystitis may be related to a defect in the high viscosity glycosaminoglycan layer on the luminal surface of the bladder, intravesical administration of the low viscosity pentosanpolysulfate does not provide adequate protection to the transitional epithelium of the urinary bladder and associated structures. Therefore, what is needed is a substance which will coat the transitional epithelium of the urinary bladder and associated structures and provide a barrier between irritants within the lumen of the urinary bladder and associated structures and the transitional epithelium lining the urinary bladder and associated structures.

Hyaluronic acid (HA) is a heteropolysaccharide consisting of alternating residues of D-glucuronic acid and N-acetylglucosamine. HA is a linear polymer with a molecular weight of up to $13 \times 10^6$ Daltons. It is found in connective tissue, in joint synovial fluid, in ocular vitreous humor, in umbilical cord, in cocks comb and is synthesized by some bacteria including, but not limited to streptococcal species. High molecular weight HA inhibits lymphocyte migration ((Balazs E. A. et al. 1973. In: Biology of Fibroblasts. Academic Press. pp. 237–252). The phagocytic and chemotactic capacities of neutrophils and leukocytes are also inhibited. (Brandt, K. D. 1974. Clinical Chemical Acta 55:307).

HA is highly viscous, highly electronegative and highly hydrophilic. The instillation of HA having an average molecular weight of not less than $2 \times 10^5$ Daltons directly into the urinary bladder and associated structures to treat interstitial cystitis in the present invention provides unexpectedly excellent results in treating interstitial cystitis in a mammal with interstitial cystitis.

SUMMARY OF THE INVENTION

Briefly, the present invention comprises a method for treating interstitial cystitis in a mammal with interstitial cystitis comprising the step of contacting the transitional epithelium lining the urinary surface of the urinary bladder and associated structures in a mammal having interstitial cystitis with a solution containing HA having an average molecular weight of not less than $2 \times 10^5$ Daltons in a concentration effective to treat the interstitial cystitis.

This invention also includes a method for treating urinary bladder trauma, urinary bladder irritation and urinary bladder infection in a mammal with bladder trauma, bladder irritation or bladder infection comprising the step of contacting the transitional epithelium lining the urinary surface of the urinary bladder and associated structures in a mammal having urinary bladder trauma, urinary bladder irritation or urinary bladder infection with a solution containing HA having an average molecular weight of not less than $2 \times 10^5$ Daltons in a concentration effective to treat the bladder trauma, bladder irritation or bladder infection.

This invention further comprehends the addition of various substances including, but not limited to, antibiotics, bacterial cell extracts, viruses, cytokines and interferons to the HA composition for use in treating interstitial cystitis, urinary bladder trauma, urinary bladder irritation and urinary bladder infection.

It is an object of the present invention to provide a method for treating interstitial cystitis in a mammal with interstitial cystitis by contacting the transitional epithelium lining the urinary surface of the urinary bladder and associated structures with a solution containing HA having an average molecular weight of not less than $2 \times 10^5$ Daltons in a concentration effective to treat the interstitial cystitis.

It is also an object of the present invention to provide a method for treating trauma, irritation or infection of the lining of the urinary bladder and associated structures in a mammal with trauma, irritation or infection of the lining of the urinary bladder and associated structures by contacting the urinary surface of the urinary bladder and associated structures with a solution containing HA having an average molecular weight of not less than $2 \times 10^5$ Daltons in a concentration effective to treat the trauma, irritation or infection of the lining of the urinary bladder and associated structures.

Other objects, features and advantages of the present invention will become apparent upon reading the following detailed description of the preferred embodiment of the invention when taken in conjunction with the appended claims.

DETAILED DESCRIPTION OF THE INVENTION

Figure 1:
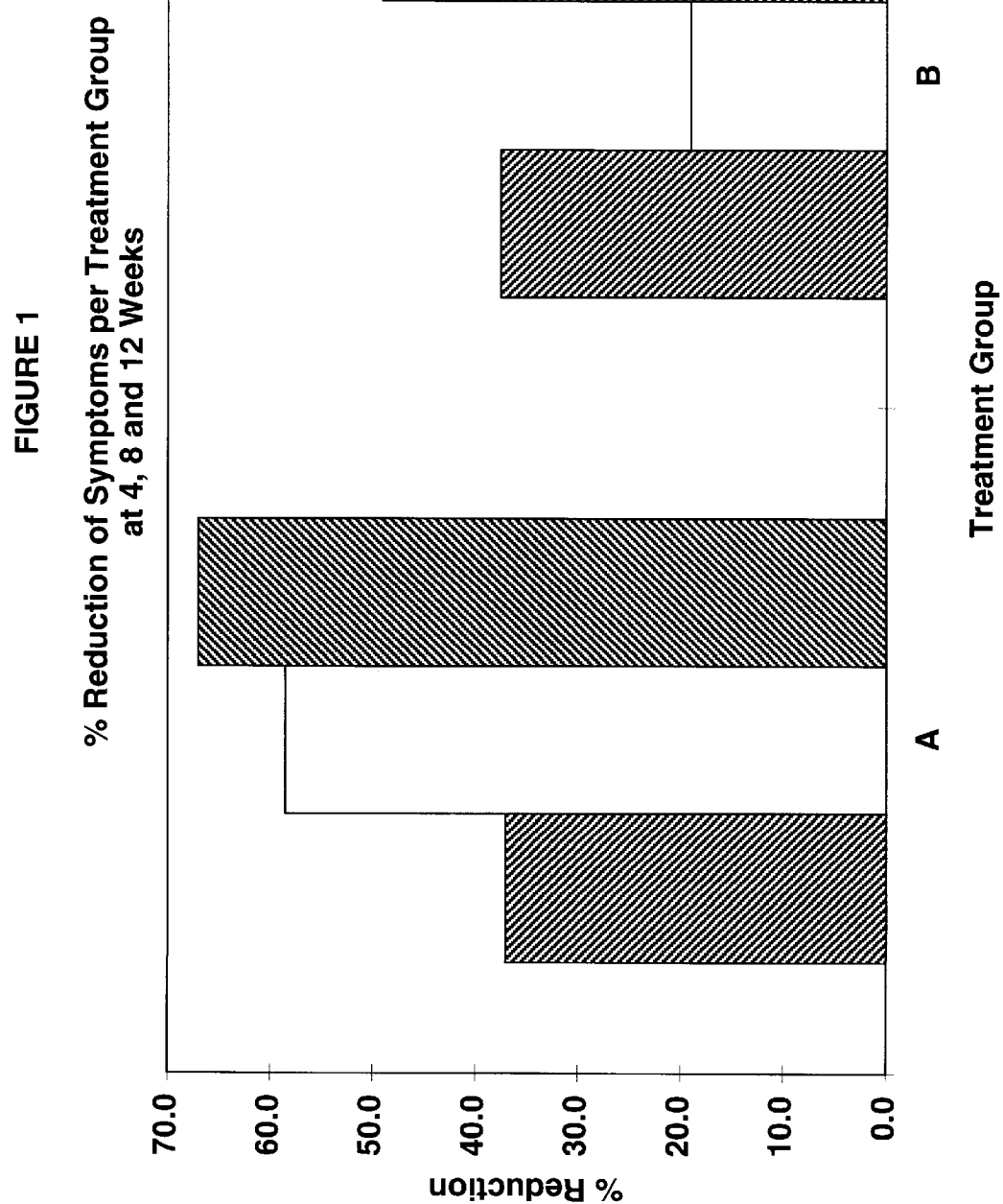
FIG. 1 shows the percent reduction of symptoms in Group A and Group B after 4, 8 and 12 weeks of HA treatment.

As used herein, the phrase "urinary surface of the bladder" refers to the transitional epithelium which lines the bladder.

As used herein, the phrase "associated structures" refers to the renal pelvis, ureters and urethra.

The present invention is directed to a method for treating interstitial cystitis in a mammal with interstitial cystitis by contacting the urinary surface of the urinary bladder and associated structures with a solution containing HA having an average molecular weight of not less than $2 \times 10^5$ Daltons in a concentration effective to treat the interstitial cystitis.

It has been discovered that HA and salts thereof, having an average molecular weight of not less than $2 \times 10^5$ Daltons, unexpectedly, is successful in treating interstitial cystitis in a mammal with interstitial cystitis.

The HA for use in this invention has an average molecular weight of not less than $2 \times 10^5$ Daltons. Preferably the HA has a molecular weight range of $5 \times 10^5$ to $3.1 \times 10^6$ Daltons. More preferably the HA has molecular weight range of $6 \times 10^5$ to $1.9 \times 10^6$ Daltons. Most preferably the HA has an average molecular weight selected from the group consisting of $6.5 \times 10^5$ Daltons, $8.7 \times 10^5$ Daltons and $1.9 \times 10^6$ Daltons.

Various methods for obtaining molecular weight fractions of HA are available. These include fractionation of HA prepared from cartilage, fractionation of HA derived from bacteria including, but not limited to, streptococcal species and purchase of molecular weight fractions of HA from commercial sources including, but not limited to, Fluka Chemical Corporation, Ronkonkoma, N.Y., Genzyme Corporation, Cambridge, Mass. and Lifecore Biomedical, Inc., Chaska, Minn..

Preferably, the HA for use in the present invention is present in a concentration from about 0.01 mg/ml to about 25 mg/ml. More preferably, the HA is present in a concentration from about 0.1 mg/ml to about 2 mg/ml. Most preferably, the HA is present in a concentration from about 0.4 mg/ml to about 1.2 mg/ml. The HA is solubilized in a pharmaceutically acceptable buffer including, but not limited to, physiological saline and phosphate buffered saline. However, it is to be understood that any of the physiological buffers known to those skilled in the art to be pharmaceutically acceptable for contacting the surface of the urinary bladder and associated structures in a mammal can be used in the present invention.

The HA solution for use in the present invention may further include an antibiotic effective for treating interstitial cystitis. Determination of the antibiotic and of the amount of the antibiotic to be included in the HA solution are well within the determination of those skilled in the art. The HA solution for use in the present invention may further include an immunotherapeutic agent including, but not limited to, bacterial cell extracts such as mycobacterial cell wall extract and bacilli calmette-guerin cell wall extract, viruses, cytokines and interferons.

Preferably, the HA solution for use in the present invention is instilled directly into the urinary bladder and associated structures. Preferably the volume of the HA solution is between approximately 5 ml and 100 ml. More preferably the volume of the HA solution is between approximately 20 ml and 70 ml. Most preferably, the volume of the HA solution is between approximately 40 and 60 ml.

Preferably, the amount of HA to be instilled directly into the bladder and associated structures in the present invention is between approximately 5 mg and 100 mg. More preferably, the amount of HA is between approximately 20 mg and 60 mg. Most preferably, the amount of HA is between approximately 35 mg and 45 mg.

Preferably, the HA solution of the present invention is administered from a container such as, but not limited to, a bottle. The HA composition may instilled directly into the urinary bladder and associated structures using a urinary catheter. However, it is to be understood that any method known to those skilled in the art for contacting the urinary surface of the urinary bladder and associated structures in a mammal with a pharmaceutical solution can be used in the present invention. These include, but are not limited to, transabdominal instillation and intravenous administration.

Preferably, the HA solution should remain in contact with the urinary bladder and associated structures for from approximately 3 minutes to 8 hours, more preferably from 10 minutes to 4 hours and most preferably from 30 minutes to 2 hours.

Treating interstitial cystitis in a mammal having interstitial cystitis with a solution containing HA by contacting the urinary bladder and associated structures with HA and salts thereof, having an average molecular weight of not less than $2 \times 10^5$ Daltons, provides unexpectedly good results in providing relief from the symptoms of interstitial cystitis without disturbing side effects.

EXAMPLE 1

Isolation, Purification and Fractionation of Hyaluronic Acid

The following describes a method for the isolation, purification and fractionation of hyaluronic acid from cartilage for use in this invention.
Pre-Treatment of Cocks Combs
The preparation of sodium hyaluronate from frozen or fresh cocks combs involves the following steps: The cocks combs are minced, homogenized, dehydrated in acetone, and vacuum dried to a dry powder. The water content of the discarded acetone is less than 2.0%. The powder is digested enzymatically with papain in a buffered aqueous medium containing cysteine hydrochloride. The resulting mixture is clarified and ultrafiltered using a membrane with a molecular weight exclusion limit of $3 \times 10^4$ Daltons. The retained clear liquid has a pH between 5.0 and 7.0. The mucopolysaccharide content is 2.0 and 6.0 mg/ml sodium hyaluronate as determined by glucuronic acid assay. The amino acid content is greater than 6.0 mg/ml as determined by ninhydrin assay.
Complexing, Fractionation, Precipitation NaCl (up to 0.1M) and cetyl-pyridinium chloride (CPC) are added to the clear liquid with agitation. The precipitate is collected by centrifugation and washed three times in 0.01M NaCl with 0.05% CPC. The precipitate is suspended in 0.05M NaCl with 0.05% CPC with agitation and the cloudy supernatant is eliminated. This procedure is repeated several times using 0.1M NaCl with 0.05% CPC. The precipitate is then dispersed in 0.3M NaCl with 0.05% CPC with agitation and the extraction is repeated three times. The precipitate is then eliminated. The clear supernatants are pooled, brought to 0.23M NaCl, CPC is added, the mixture is treated with Celite(R), and filtered. After Celite(R) treatment, the sodium hyaluronate content is 2.5–5.0 mg/ml as determined by glucuronic acid assay.
Isolation of Hyaluronic Acid The filtrate is ultrafiltered using a membrane with a molecular weight exclusion limit of $3 \times 10^4$ Daltons and the retained liquid is concentrated. This liquid is precipitated with 95% ethanol and centrifuged. The precipitate is dissolved in 0.1M NaCl and precipitated again with 95% ethanol. The precipitate is collected and washed yielding a crude product having an average molecular weight of not less than $2.5 \times 10^5$ Daltons. The yield is equivalent to 0.6% of original fresh tissue.
Purification of Hyaluronic Acid Fraction The precipitate is dissolved in pyrogen-free distilled water (10 mg/ml) and ultrafiltered using a membrane with a molecular weight exclusion limit of $2 \times 10^5$ Daltons without addition of supplementary water. This increases the concentration of molecules having a molecular weight greater than $2 \times 10^5$ Daltons. Ultrafiltration is used to reduce the volume to 10% of original volume. Water is added to the concentrated solution and the operation is repeated twice. The concentrated solution is collected and is diluted with water to a concentration of 5 mg/ml hyaluronic acid. NaCl is added to-bring the solution to 0.1M and the solution is precipitated with four volumes of 95% ethanol. The precipitate is washed and then vacuum dried.

This purified hyaluronic acid is polydisperse and has an average molecular weight, of not less than $2 \times 10^5$ Daltons. Methods for further fractionating this HA into different molecular weight fractions are well known to those of ordinary skill in this art. Further methods for preparing purified HA of the molecular weights claimed in this invention are disclosed in U.S. Pat. No. 4,141,973 to Balzas which is incorporated by reference.

EXAMPLE 2

Interstitial Cystitis Pilot Study

In this pilot study five patients with interstitial cystitis, receive instillation directly into the urinary bladder and associated structures of 40 mg of hyaluronic acid having an average molecular weight of $6.5 \times 10^5$ Daltons in 40 ml to 70 ml sterile saline (USP).

Outcome criteria for this pilot study are related to improvement of symptoms based on decreases in pre-therapy symptoms, pre-therapy pain, and pre-therapy urgency.

Subject 1

Patient JM

Interstitial cystitis patient JM (#002) fails treatment with both direct instillation of heparin into the urinary bladder and associated structures and oral pentosanpolysulfate. JM is treated according to the study protocol. Forty mg of HA having an average molecular weight of $6.5 \times 10^5$ Daltons (range $5 \times 10^5$ to $7.3 \times 10^5$ Daltons) in 50 ml of normal saline (USP) is instilled directly into the urinary bladder under sterile conditions using a urethral catheter. The catheter is removed and the HA solution is maintained in the bladder for 30 minutes. The treatment is repeated weekly for 7 weeks After the 7th treatment, the patient reports a marked improvement in suprapubic pain and in urgency of urination. The treatment is repeated 4 times during the following 17 weeks. After the last treatment, the patient reports a 100% improvement in suprapubic pain and improvement in urgency. No side effects of the HA treatment are reported by the patient.

Subject 2

Patient GH

Interstitial cystitis patient GH (#003) fails treatment with oral propantheline bromide (2-hydroxyethyl)-diisopropylmethyl ammonium bromide xanthene-9-carboxylate, phenylpropanolamine hydrochloridene and guaifenesin. GH is treated according to the study protocol. Forty mg of HA having an average molecular weight of $6.5 \times 10^5$ Daltons in 50 ml of normal saline (USP) is instilled directly into the urinary bladder and associated structures under sterile conditions using a urethral catheter. The catheter is removed and the HA solution is maintained in the bladder for 60 minutes. The treatment is repeated 4 times during an approximately 12 week period. After the last treatment, the patient reports a 100% improvement in pre-therapy symptoms, pre-therapy pain and pre-therapy urgency. No side effects of the HA treatment are reported by the patient.

Subject 3

Patient LB

Interstitial cystitis patient LB (#001) fails treatment with direct instillation of DMSO and heparin into the urinary bladder and associated structures. LB is treated according to the study protocol. Forty mg of HA having an average molecular weight of $6.5 \times 10^5$ Daltons in 50 ml of normal saline (USP) is instilled directly into the urinary bladder and associated structures under sterile conditions using a urethral catheter. The catheter is removed and the HA solution is maintained in the bladder for 45 minutes. The treatment is repeated weekly for 5 weeks with significant improvement in pre-therapy symptoms, pre-therapy pain and pre-therapy urgency. Due to an unrelated illness, treatment is interrupted for approximately 7 weeks and symptoms return. After two subsequent treatments, the patient is again improved. Again, due to an unrelated illness, treatment is interrupted for 13 weeks and symptoms return. After two subsequent treatments, the patient reports no improvement in symptoms and treatment is discontinued at the patient's request.

Subject 4

Patient MM

Interstitial cystitis patient MM (#004) is treated according to the study protocol. Forty mg of HA having an average molecular weight of $6.5 \times 10^5$ Daltons in 50 ml of normal saline (USP) is instilled directly into the urinary bladder and associated structures under sterile conditions using a urethral catheter. The catheter is removed and the HA solution is maintained in the bladder for 50 minutes. The treatment is repeated 9 times over a 22 week period. After the last treatment, the patient reports improvement in pre-therapy symptoms, in pre-therapy pain and in pre-therapy urgency. Although the patient reports no side effects from the HA treatment, the patient elects to discontinue HA treatment.

Subject 5

Patient MS

Interstitial cystitis patient MS (#006) is treated according to the study protocol. Forty mg of HA having an average molecular weight of $6.5 \times 10^5$ Daltons in 50 ml of normal saline (USP) is instilled directly into the urinary bladder and associated structures under sterile conditions using a urethral catheter. The catheter is removed and the HA solution is maintained in the bladder for 60 minutes. The treatment is repeated weekly for 7 weeks. At the end of the 7th week there is a marked improvement in pre-therapy symptoms, in pre-therapy pain and in pre-therapy urgency. Four maintenance treatments are given during the following 16 months. Throughout and at the end of each of the maintenance treatments, the marked improvement is maintained.

EXAMPLE 3

Interstitial Cystitis Study

Hyaluronic acid (HA) is used to treat interstitial cystitis according to the present invention. Twenty-four humans, each having interstitial cystitis, are treated with HA (sodium hyaluronate) having an average molecular weight of $6.5 \times 10^5$ Daltons.

Inclusion Criteria for this Study Include:
1. $\geq 18$ years of age
2. diagnosis of interstitial cystitis
3. untreated or failure of previous treatment
4. two or more of following findings present: a) suprapubic, urethral, or perineal pain; b) chronic inflammation or mast cell infiltration on cystoscopy or biopsy with no evidence of malignancy; c) hydrodistension under anesthesia to 80 to 100 cm $H_2O$ pressure with glomerulations (multiple petechiae), bloody effluent and diminished bladder capacity; d) sterile urine cultures; e) decreased compliance on cystometrogram; f) pain on bladder filling (diminished by emptying)

Exclusion Criteria for this Study Include:
1. benign or malignant bladder tumors
2. evidence of vesicoureteral reflux or urethral diverticulum
3. uterine, cervical, vaginal or urethral cancer
4. UTI, vaginitis, prostatitis
5. bladder or lower ureteral calculi, active herpes (herpes virus type II)
7. positive urine cytology
8. cystometrogram capacity >400 cc, absence of sensory urgency or unstable bladder 9. waking frequency <5 in 12 hours
10. neurogenic bladder dysfunction
11. patients taking any medication or active treatment for interstitial cystitis treatment within 30 days of enrollment in study
12. prior urinary diversion
13. pregnant women Assessment Criteria for this Study Include:

Pre-treatment symptoms and the effects of HA treatment are assessed using a quality of life symptom score, a visual analog (VAS) pain scale, a visual analog (VAS) urgency scale and a 72 hour voiding record.

Outcome Criteria for this Study Include:
1. Complete Response (CR): Improvement of symptoms with a ≧90% decrease in pre-therapy symptom score, VAS pain scale, VAS urgency scale and patient does not require medication.
2. Partial Response (PR): Incomplete resolution of symptoms with ≧50% decrease in pre-therapy symptom score, VAS pain scale, VAS urgency scale and patient continues to require medication for complete relief of symptoms.
3. Minor Response (MR): Incomplete resolution of symptoms with <50% decrease in pre-therapy symptom score, VAS pain scale, VAS urgency scale and patient continues to require medication for partial relief of symptoms.
4. Failure (F): No improvement in symptoms.
5. Withdrawal (WD): Patient withdraws or is withdrawn from the study.

Treatment Protocols for this Study Include:

Each patient receives direct instillation into the urinary bladder and associated structures of HA having an average molecular weight of $6.5 \times 10^5$ Daltons. Under sterile conditions, a urethral catheter is introduced into the urinary bladder and any residual urine is removed and sent for bacterial culture. Fifty ml containing 40 mg of the HA composition is instilled directly into the urinary bladder through the urethral catheter and the catheter is removed. The patient is asked to retain the HA solution as long as possible.

The HA instillation is given 1x/week for 4 weeks (induction). If the patient's symptoms completely resolve within the 4 week induction period, treatment is given monthly to the end of 12 months (maintenance). If the patient's symptoms partially resolve within the 4 week induction period, the patient is retreated 1x/week for 4 weeks. If after retreatment the patient's symptoms completely resolve, maintenance treatment is given. If the patient's symptoms do not resolve at all within the 4 week induction period, treatment is discontinued and the patient is withdrawn from the study.

Results obtained are shown in Table I and in Table II.

Table I shows results from 14 patients entering the study at various times within the study protocol. Twelve of the 14 patients show either a complete response or a partial response to the HA treatment after from 4 to 28 weeks of treatment. Two of the 14 patients show no response to the HA treatment after 8 weeks of treatment.

TABLE I

HYALURONIC ACID (HA) TREATMENT OF INTERSTITIAL CYSTITIS

| Patient # | Date of 1st Tx (m/d/y) | Week 4 | Week 8 | Week 12 | Week 16 | Week 20 | Week 24 | Week 28 | Week 32 | Week 38 | Week 48 |
|---|---|---|---|---|---|---|---|---|---|---|---|
| 01 | 940615 | CR | PR | PR | CR | CR | CR | CR | | | |
| 02 | 940728 | PR | CR | PR | CR | PR | | | | | |
| 03 | 940802 | | F | PR | PR | | | | | | |
| 04 | 940916 | F | PR | F | PR | | | | | | |
| 06 | 941004 | | F | PR | | | | | | | |
| 07 | 941005 | F | PR | PR | | | | | | | |
| 08 | 941007 | F | PR | | | | | | | | |
| 09 | 941027 | | PR | | | | | | | | |
| 10 | 941026 | PR | PR | CR | | | | | | | |
| 11 | 941106 | F | F | | | | | | | | |
| 12 | 941107 | PR | PR | CR | | | | | | | |
| 13 | 941108 | CR | CR | CR | | | | | | | |
| 14 | 941118 | F | CR | | | | | | | | |
| 15 | 941222 | F | F | | | | | | | | |

Table II shows results for 24 patients completing 24 weeks, 23 patients completing 32 weeks, 20 patients completing 40 weeks, and 16 patients completing 48 weeks of the HA treatment protocol. At the end of the induction period(week 4), 4 patients show a complete response, 10 a partial response, 9 a minor response and 1 no response to the HA treatment. One patient does not complete the induction period. Of the 18 patients remaining in the study after 24 weeks of HA treatment, 6 show a complete response, 6 a partial response, 4 a minor response, and 2 no response. Of the 9 patients remaining in the study after 48 weeks of HA treatment, 2 show a complete response, 6 a partial response and 1 a minor response. Of the 7 patients who withdraw from the study, 3 withdraw for treatment failure and 4 are withdrawn for protocol violations.

TABLE II

RESPONSE RATES TO HYALURONIC ACID (HA) TREATMENT OF INTERSTITIAL CYSTITIS

| Week # | 4 | 8 | 12 | 16 | 20 | 24 | 32 | 40 | 48 |
|---|---|---|---|---|---|---|---|---|---|
| # of patients | 25 | 24 | 24 | 24 | 24 | 24 | 23 | 20 | 16 |
| CR | 4 | 4 | 6 | 6 | 6 | 6 | 4 | 4 | 2 |
|  | (16%) | (17%) | (25%) | (26%) | (25%) | (25%) | (17%) | (20%) | (13%) |
| PR | 10 | 12 | 11 | 11 | 11 | 6 | 8 | 6 | 6 |
|  | (40%) | (50%) | (46%) | (46%) | (46%) | (25%) | (35%) | (30%) | (37%) |
| MR | 9 | 7 | 5 | 4 | 2 | 4 | 4 | 2 | 1 |
|  | (36%) | (29%) | (21%) | (17%) | (8%) | (17%) | (17%) | (10%) | (6%) |
| F | 1 | 1 | 1 | 1 | i | 2 | 0 | 0 | 0 |
|  | (4%) | (4%) | (4%) | (4%) | (4%) | (8%) | (0%) | (0%) | (0%) |
| WID | 1 | 0 | 1 | 2 | 4 | 6 | 7 | 7 | 7 |
|  | (4%) | (0%) | (4%) | (8%) | (17%) | (25%) | (30%) | (35%) | (44%) |

The data in Table I and in Table II show that direct instillation into the urinary bladder and associated structures of a solution containing HA having an average molecular weight of $6.5 \times 10^5$ Daltons is unexpectedly effective in relieving the symptoms of interstitial cystitis. That is, the method of treating interstitial cystitis HA of the present invention results in unexpected and significant improvement in pre-therapy symptoms, pre-therapy pain and pre-therapy urgency.

EXAMPLE 4

An interstitial cystitis patient is treated according to the following protocol. Forty mg of HA having an average molecular weight of $8.7 \times 10^5$ Daltons in 50 ml of normal saline (USP) is instilled directly into the urinary bladder under sterile conditions using a urethral catheter. The catheter is removed and the HA solution is maintained in the bladder for 60 minutes. The treatment is repeated weekly and there is a marked improvement in pre-therapy symptoms, in pre-therapy pain and in pre-therapy urgency.

EXAMPLE 5

An interstitial cystitis patient is treated according to the following protocol. Forty mg of HA having an average molecular weight of approximately $1.9 \times 10^6$ Daltons in 50 ml of normal saline (USP) is instilled directly into the urinary bladder and associated structures under sterile conditions using a urethral catheter. The catheter is removed and the HA solution is maintained in the bladder for 60 minutes. The treatment is repeated weekly and there is a marked improvement in pre-therapy symptoms, in pre-therapy pain and in pre-therapy urgency.

EXAMPLE 6

Interstitial Cystitis Study

Hyaluronic acid (HA) is used to treat interstitial cystitis in humans having interstitial cystitis according to the present invention. Each patient in this study meets the criteria established by the National Institute of Arthritis, Diabetes, Digestive and Kidney Diseases (NIDDK) for having interstitial cystitis.

Inclusion Criteria for this Study Include:
1. $\geq 18$ years of age
2. diagnosis of interstitial cystitis
3. untreated or failure of previous treatment
4. score of $\geq 6$ on a pre-therapy Symptom Evaluation Score
5. score of $\geq 4$ on a pre-therapy VAS Pain Scale
6. score of $\geq 4$ on a pre-therapy VAS Urgency Scale Exclusion Criteria for this Study Include:
1. bladder capacity >350 cc on awake cystometry
2. duration of symptoms <9 months
3. absence of nocturia
4. symptoms relieved by antimicrobials, urinary antiseptics, anticholinergics or antispasmodics
5. waking frequency <8 in 24 hours
6. bacterial cystitis or prostatitis within a three-month period
7. bladder or lower ureteral calculi, active genital herpes
8. uterine, cervical, vaginal or urethral cancer
9. chemical, tuberculous or radiation cystitis
10. benign or malignant bladder tumors
11. neurogenic bladder dysfunction
12. patients taking any medication or active treatment for interstitial cystitis within 30 days of enrollment in study
13. prior urinary diversion
14. pregnant women Assessment Criteria for this Study Include:
Pre-treatment symptoms and the effects of HA treatment are assessed using a quality of life questionnaire, a symptom evaluation score, a visual analog (VAS) pain scale, a visual analog (VAS) urgency scale and a 72 hour voiding record.

Outcome Criteria for this Study Include:
1. Complete Response (CR): Improvement of symptoms with a 75% decrease in pre-therapy symptom evaluation score, pre-therapy VAS pain scale and pre-therapy VAS urgency scale.
2. Partial Response (PR): Incomplete resolution of symptoms and a 50–74.99% decrease in pre-therapy symptom evaluation score, pre-therapy VAS pain scale and pre-therapy VAS urgency scale.
3. Minor Response (MR) Incomplete resolution of symptoms with a <50% decrease in pre-therapy symptom evaluation score, pre-therapy VAS pain scale and pre-therapy VAS urgency scale.
4. Failure (F): No improvement in symptoms. 5. Withdrawal (WD). Patient withdraws or is withdrawn from the study.

Treatment Protocols for this Study Include:
Eleven humans, each having interstitial cystitis, are assigned sequentially to receive direct instillation into the urinary bladder and associated structures of HA having an average molecular weight of $8.7 \times 10^5$ Daltons (Group A) or 1.9×10⁶ Daltons (Group B). Under sterile conditions, a urethral catheter is introduced into the urinary bladder and any residual urine is removed and sent for bacterial culture. Fifty ml of normal saline (USP) containing 40 mg of Group A HA or of Group B HA is instilled directly into the urinary bladder through the urethral catheter and the catheter is removed. The patient is asked to retain the HA solution as long as possible.

The HA instillation is given 1×/week for 4 weeks (induction) followed by 1×/4 weeks for 8 weeks (maintenance). Therapy is discontinued at 12 weeks after the first HA instillation. The efficacy of HA in the treatment of interstitial cystitis is assessed at 4, 8 and 12 weeks after the first HA instillation using a symptom evaluation score, a VAS pain scale and a VAS urgency scale.

Results for the 11 patients entering the study at various times within the study period are shown in Table III, Table IV, Table V and FIG. 1.

Table III shows the response of each patient in Group A and in Group B to HA treatment after 4, 8 and 12 weeks. The assessment of response is based on calculating the average of the three scores: symptom evaluation score, VAS pain scale and VAS urgency scale. These data show that HA having average molecular weights of $8.7 \times 10^5$ Daltons (Group A) and of $1.9 \times 10^6$ Daltons (Group B) are effective in relieving the symptoms of interstitial cystitis in a majority of the patients treated.

TABLE III

HYALURONIC ACID (HA) TREATMENT OF INTERSTITIAL CYSTITIS

| Patient # | Treatment | Week 4 | Week 8 | Week 12 |
|---|---|---|---|---|
| 1001 | A | MR | CR | CR |
| 1002 | B | F | F | MR |
| 1003 | B | PR | F | PR |
| 2001 | A | MR | MR | MR |
| 2002 | B | PR | PR | PR |
| 2003 | A | F | MR | PR |
| 2004 | B | MR | MR | MR |
| 2005 | A | PR | CR | |
| 2006 | B | PR | MR | |
| 2007 | A | MR | | |
| 2008 | B | MR | | |

Table IV shows the absolute values obtained on the symptom evaluation score (SS), the VAS pain scale (P) and the VAS urgency scale (U) prior to treatment (week 0), at the end of the induction period (week 4) and after weeks 8 and 12 of maintenance treatment. At the end of the 4 week induction period, complete data is available for 11 patients in the study. Of these 11, 4 in group A and 5 in Group B show an improvement in the average % (SS+P+U). One patient in Group A and 1 in Group B show an increase in symptoms after 4 weeks of HA treatment. Of 7 patients completing the 8 week maintenance period (week 12), each shows an improvement in the average % (SS+P+U). Of these 7, 3 are in Group A and 4 are in Group B.

TABLE IV

EVALUATION OF THE EFFICACY OF HYALURONIC ACID IN THE TREATMENT OF INTERSTITIAL CYSTITIS

| Patient # | Week 0 | | | Week 4 | | | | | | Average % | Week 8 | | |
|---|---|---|---|---|---|---|---|---|---|---|---|---|---|
| | SS | P | U | SS | % | P | % | U | % | (SS + P + U) | SS | % | P |
| 1001A | 8 | 5.93 | 4.86 | 7 | 13 | 1.46 | 75 | 2.20 | 85 | 48 | 2.00 | 75 | 0.00 |
| 1002B | 8 | 9.46 | 6.06 | 8 | −12 | 8.30 | 12 | 7.13 | −18 | −6 | 9.00 | −13 | 8.30 |
| 1003B | 8 | 4.10 | 4.66 | 5 | 38 | 0.60 | 85 | 0.60 | 87 | 70 | 8.00 | 0 | 4.93 |
| 2001A | 10 | 8.66 | 8.06 | 7 | 30 | 5.23 | 17 | 5.23 | 30 | 28 | 8.00 | 20 | 5.16 |
| 2002B | 10 | 8.26 | 8.66 | 5 | 66 | 2.66 | 65 | 3.30 | 62 | 69 | 4.00 | 60 | 2.13 |
| 2003A | 8 | 7.00 | 5.20 | 7 | 22 | 6.66 | 5 | 7.26 | −40 | −4 | 7.00 | 22 | 4.93 |
| 2004B | 12 | 6.66 | 8.58 | 12 | 17 | 5.93 | 32 | 5.43 | 37 | 28 | 10.00 | 17 | 5.93 |
| 2005A | 8 | 7.00 | 7.93 | 4 | 50 | 1.20 | 83 | 3.16 | 60 | 64 | 1.00 | 88 | 0.00 |
| 2006B | 8 | 5.70 | 7.76 | 5 | 38 | 1.46 | 74 | 3.53 | 65 | 55 | 5.00 | 38 | 5.70 |
| 7007A | 8 | 7.06 | 5.73 | 5 | 38 | 3.06 | 57 | 2.76 | 52 | 49 | | | |
| 2008B | 9 | 8.20 | 8.20 | 10 | −11 | 7.20 | 12 | 4.93 | 40 | 14 | | | |

| Patient # | Week 8 | | Average % | Week 12 | | | | | | Average % |
|---|---|---|---|---|---|---|---|---|---|---|
| | % | U | % | (SS + P + U) | SS | % | P | % | U | % | (SS + P + U) |
| 1001A | 100 | 0.00 | 100 | 92 | 2.00 | 76 | 0.03 | 99 | 0.03 | 99 | 91 |
| 1002B | 12 | 7.13 | −18 | −6 | 8.00 | 0 | 0.43 | 8S | 4.61 | 21 | 39 |
| 1003B | −20 | 7.23 | −55 | −25 | 4.00 | 60 | 1.46 | 84 | 1.78 | 62 | 59 |
| 2001A | 23 | 4.82 | 40 | 27 | 8.00 | 40 | 3.88 | 42 | 3.86 | 51 | 44 |
| 2002B | 74 | 3.48 | 61 | 65 | 5.00 | 50 | 1.82 | 81 | 2.33 | 73 | 68 |
| 2003A | 30 | 5.02 | 3 | 18 | 4.00 | 56 | 1.82 | 73 | 1.96 | 62 | 64 |
| 2004B | 32 | 5.43 | 37 | 28 | 7.00 | 42 | 6 83 | 23 | 7.80 | 9 | 27 |
| 2005A | 100 | 0.46 | 94 | 94 | | | | | | | |
| 2006B | 0 | 3.63 | 63 | 30 | | | | | | | |
| 7007A | | | | | | | | | | | |
| 2008B | | | | | | | | | | | |

(−) values indicate an increase in symptoms.

Table V shows the mean ± standard deviation of the percent change from pre-therapy symptoms in the symptom score, the VAS pain scale and the VAS urgency scale for Group A and for Group B patients after 4, 8 and 12 weeks of treatment. Patients in both of the treatment groups, Group A and Group B, show a decrease in pre-therapy symptoms when treated according to the HA method of the present invention.

TABLE V

PERCENT CHANGE FROM BASELINE IN
PATIENT ASSESSMENT BY TREATMENT GROUP

|  |  | A | | | B | | |
|---|---|---|---|---|---|---|---|
|  |  | n | Mean | S.D. | n | Mean | S.D. |
| Symptom Score | Week 4 | 5 | −30.4 | 14.3 | 6 | −19.7 | 26.6 |
|  | Week 8 | 4 | −51.2 | 35.1 | 5 | −20.3 | 29.0 |
|  | Week 12 | 3 | −58.9 | 17.5 | 4 | −35.4 | 23.9 |
| Pain | Week 4 | 5 | 47.2 | 34.7 | 6 | −46.9 | 32.3 |
|  | Week 8 | 4 | −63.0 | 42.8 | 5 | −19.6 | 35.9 |
|  | Week 12 | 3 | −71.5 | 28.5 | 4 | −68.0 | 27.4 |
| Urgency | Week 4 | 5 | −32.4 | 41.4 | 6 | −43.7 | 35.1 |
|  | Week 8 | 4 | −59.3 | 46.2 | 5 | −15.5 | 50.0 |
|  | Week 12 | 3 | −70.9 | 25.4 | 4 | −41.2 | 31.2 |

(−) values Indicate a decrease in symptoms.

FIG. 1 shows graphically the percent reduction in pre-therapy symptoms in Group A patients and in Group B patients after 4, 8 and 12 weeks of HA treatment.

The data in Tables I–V and in FIG. 1 demonstrate that, in patients having interstitial cystitis, contacting the urinary bladder and associated structures with HA according to the present invention results in unexpected and significant improvement in pre-therapy symptoms, in pre-therapy pain and in pre-therapy urgency. These data also show that each of the HA solutions used, $6.5 \times 10^5$ Daltons, $8.7 \times 10^5$ Daltons and $1.9 \times 10^6$ Daltons, are unexpectedly effective in treating interstitial cystitis.

Although the invention has been described to reference to particular means, materials and examples, it is to be understood that the invention is not limited to the particulars disclosed and extends to all equivalents within the scope of the claims.

We claim:

1. A method of treating interstitial cystitis comprising the step of instilling directly into the urinary bladder and associated structures of a mammal having interstitial cystitis a solution containing hyaluronic acid having an average molecular weight of not less than $2 \times 10^5$ Daltons in a concentration effective to treat the interstitial cystitis.

2. The method of claim 1, wherein the hyaluronic acid has a molecular weight range of $5 \times 10^5$ to $3.1 \times 10^6$ Daltons.

3. The method of claim 2, wherein the hyaluronic acid has a molecular weight range of $6 \times 10^5$ to $1.2 \times 10^6$ Daltons.

4. The method of claim 3, wherein the hyaluronic acid has an average molecular weight of $6.5 \times 10^5$ Daltons.

5. The method of claim 3, wherein the hyaluronic acid has an average molecular weight of $8.7 \times 10^5$ Daltons.

6. The method of claim 2, wherein the hyaluronic acid has a molecular weight range of $1.2 \times 10^6$ to $3.1 \times 10^6$ Daltons.

7. The method of claim 6, wherein the hyaluronic acid has an average molecular weight of $1.9 \times 10^6$ Daltons.

* * * * *